United States Patent
Jang et al.

(10) Patent No.: US 12,317,922 B2
(45) Date of Patent: Jun. 3, 2025

(54) ULTRASONIC-BASED AEROSOL GENERATION DEVICE AND CARTRIDGE RECOGNITION METHOD THEREOF

(71) Applicant: KT&G CORPORATION, Daejeon (KR)

(72) Inventors: Chul Ho Jang, Daejeon (KR); Gyoung Min Go, Daejeon (KR); Hyung Jin Bae, Daejeon (KR); Jang Won Seo, Daejeon (KR); Min Seok Jeong, Daejeon (KR); Jong Seong Jeong, Daejeon (KR); Jin Chul Jung, Daejeon (KR)

(73) Assignee: KT&G CORPORATION, Daejeon (KR)

( * ) Notice: Subject to any disclaimer, the term of this patent is extended or adjusted under 35 U.S.C. 154(b) by 369 days.

(21) Appl. No.: 17/791,461

(22) PCT Filed: Jul. 13, 2021

(86) PCT No.: PCT/KR2021/008927
§ 371 (c)(1),
(2) Date: Jul. 7, 2022

(87) PCT Pub. No.: WO2022/045578
PCT Pub. Date: Mar. 3, 2022

(65) Prior Publication Data
US 2023/0030615 A1    Feb. 2, 2023

(30) Foreign Application Priority Data
Aug. 26, 2020 (KR) .................. 10-2020-0107927

(51) Int. Cl.
*A24F 40/05* (2020.01)
*A24F 40/10* (2020.01)
(Continued)

(52) U.S. Cl.
CPC .............. *A24F 40/05* (2020.01); *A24F 40/10* (2020.01); *A24F 40/42* (2020.01); *A24F 40/485* (2020.01); *A24F 40/53* (2020.01); *B05B 17/0684* (2013.01)

(58) Field of Classification Search
CPC ........ A24F 40/05; A24F 40/53; A24F 40/485; A24F 40/10; A24F 40/42; B05B 17/0684
(Continued)

(56) References Cited

U.S. PATENT DOCUMENTS

| 10,028,535 B2 | 7/2018 | Mironov |
| 2018/0318530 A1 | 11/2018 | Liu et al. |

(Continued)

FOREIGN PATENT DOCUMENTS

| CN | 204742639 U | 11/2015 |
| CN | 208909133 U | 5/2019 |

(Continued)

OTHER PUBLICATIONS

International Search Report for PCT/KR2021/008927 dated Nov. 1, 2021 [PCT/ISA/210].

(Continued)

*Primary Examiner* — Gary F Paumen
(74) *Attorney, Agent, or Firm* — Sughrue Mion, PLLC

(57) ABSTRACT

Provided herein are an ultrasonic-based aerosol generation device, which is capable of reducing cartridge replacement costs and ensuring immediate aerosol generation, and a cartridge recognition method thereof. The ultrasonic-based aerosol generation device according to some embodiments of the present disclosure may include a liquid reservoir configured to store a liquid aerosol-forming substrate, a vibration element configured to provide ultrasonic vibrations to the stored liquid aerosol-forming substrate to form an aerosol, and a porous member which is disposed to be (Continued)

spaced apart from the vibration element and has a plurality of holes formed therein. Here, the liquid aerosol-forming substrate may be pushed in a direction toward the porous member due to ultrasonic vibrations of the vibration element, and the pushed liquid may be rapidly vaporized by passing through the plurality of holes. Accordingly, an aerosol can be generated immediately upon a puff.

10 Claims, 10 Drawing Sheets

(51) Int. Cl.
*A24F 40/42* (2020.01)
*A24F 40/485* (2020.01)
*A24F 40/53* (2020.01)
*B05B 17/06* (2006.01)

(58) Field of Classification Search
USPC .......................................................... 131/329
See application file for complete search history.

(56) References Cited

U.S. PATENT DOCUMENTS

| | | | |
|---|---|---|---|
| 2019/0015612 A1 | 1/2019 | Marmur et al. | |
| 2019/0183176 A1 | 6/2019 | Liu et al. | |
| 2020/0093185 A1 | 3/2020 | Lim | |
| 2020/0146361 A1 | 5/2020 | Silver et al. | |
| 2021/0077751 A1 | 3/2021 | Hua et al. | |

FOREIGN PATENT DOCUMENTS

| | | | | |
|---|---|---|---|---|
| EP | 3 298 912 A1 | | 3/2018 | |
| EP | 3 434 120 A1 | | 1/2019 | |
| JP | 5-49067 U | | 6/1993 | |
| JP | 2015-505474 A | | 2/2015 | |
| JP | 2016-189922 A | | 11/2016 | |
| JP | 2019-515689 A | | 6/2019 | |
| KR | 10-2010-0080308 A | | 7/2010 | |
| KR | 20-2014-0002296 U | | 4/2014 | |
| KR | 10-2014-0125827 A | | 10/2014 | |
| KR | 10-2018-0079298 | * | 7/2018 | ............. A24F 47/00 |
| KR | 10-2020-0005160 A | | 1/2020 | |
| KR | 10-2020-0083458 A | | 7/2020 | |
| WO | 2019/242746 A1 | | 12/2019 | |
| WO | 2020/048008 A1 | | 3/2020 | |

OTHER PUBLICATIONS

European Search Report for EP 21 79 9159 dated Jun. 17, 2022.
Office Action dated Aug. 29, 2022 issued by the Korean Patent Office in Korean Application No. 10-2020-0107927.
Office Action issued Mar. 3, 2023 in Korean Application No. 10-2020-0107927.
Office Action issued Dec. 13, 2022 in Japanese Application No. 2021-564375.

* cited by examiner

[FIG. 1]
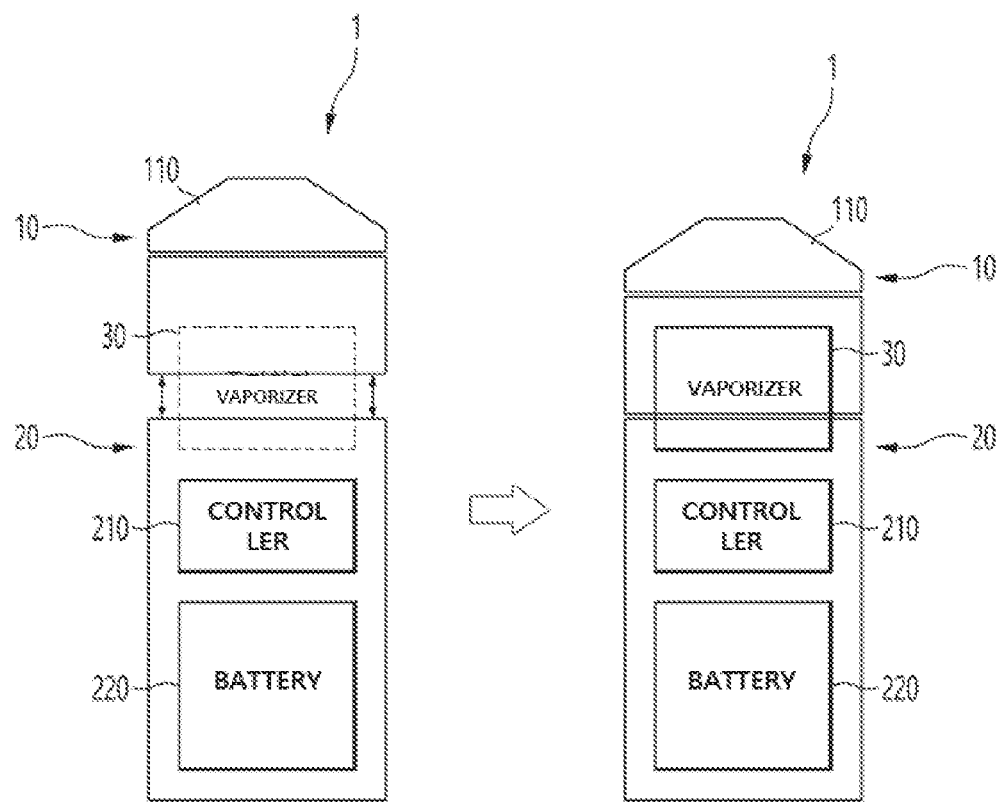

[FIG. 2]
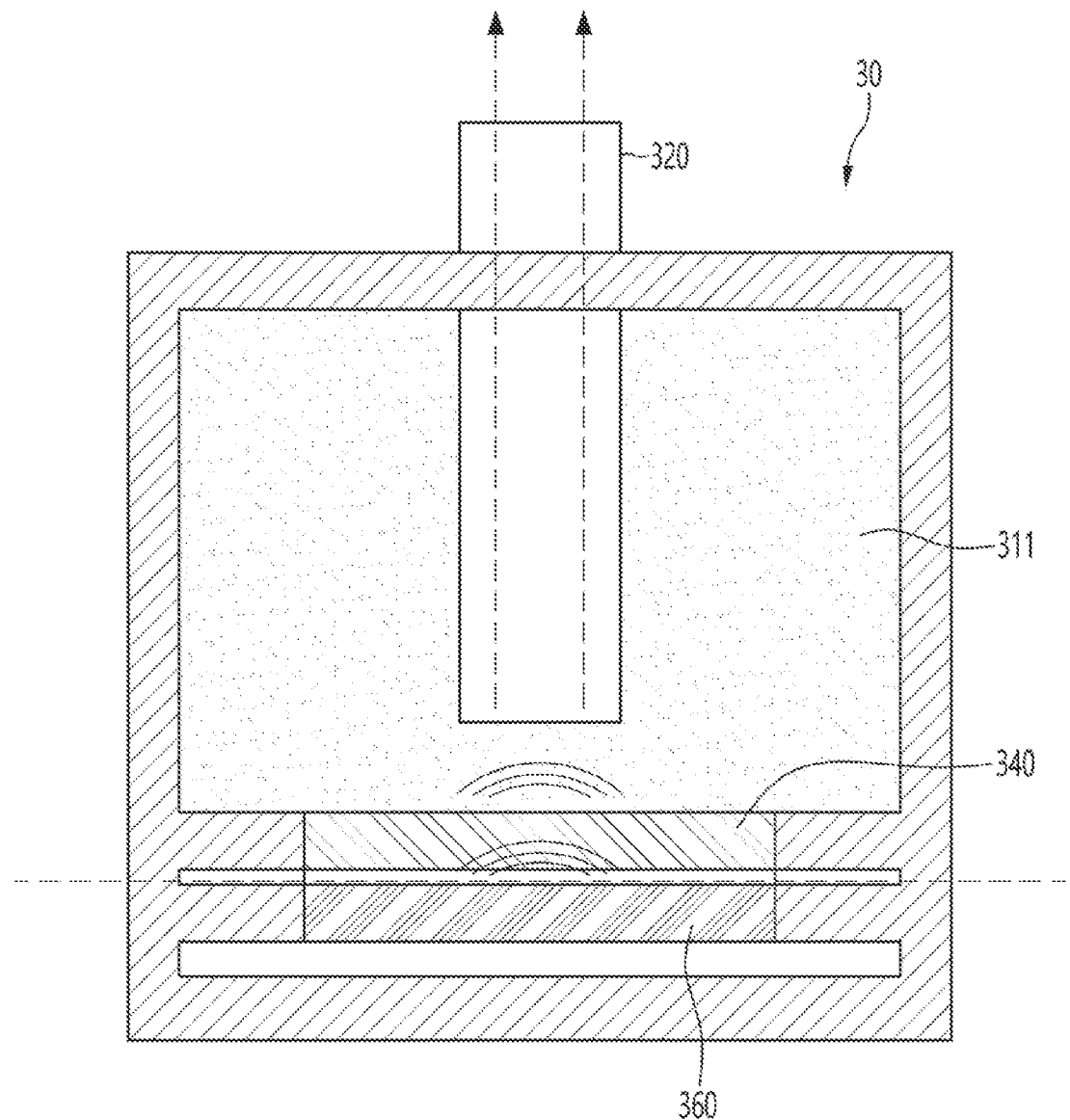

[FIG. 3]
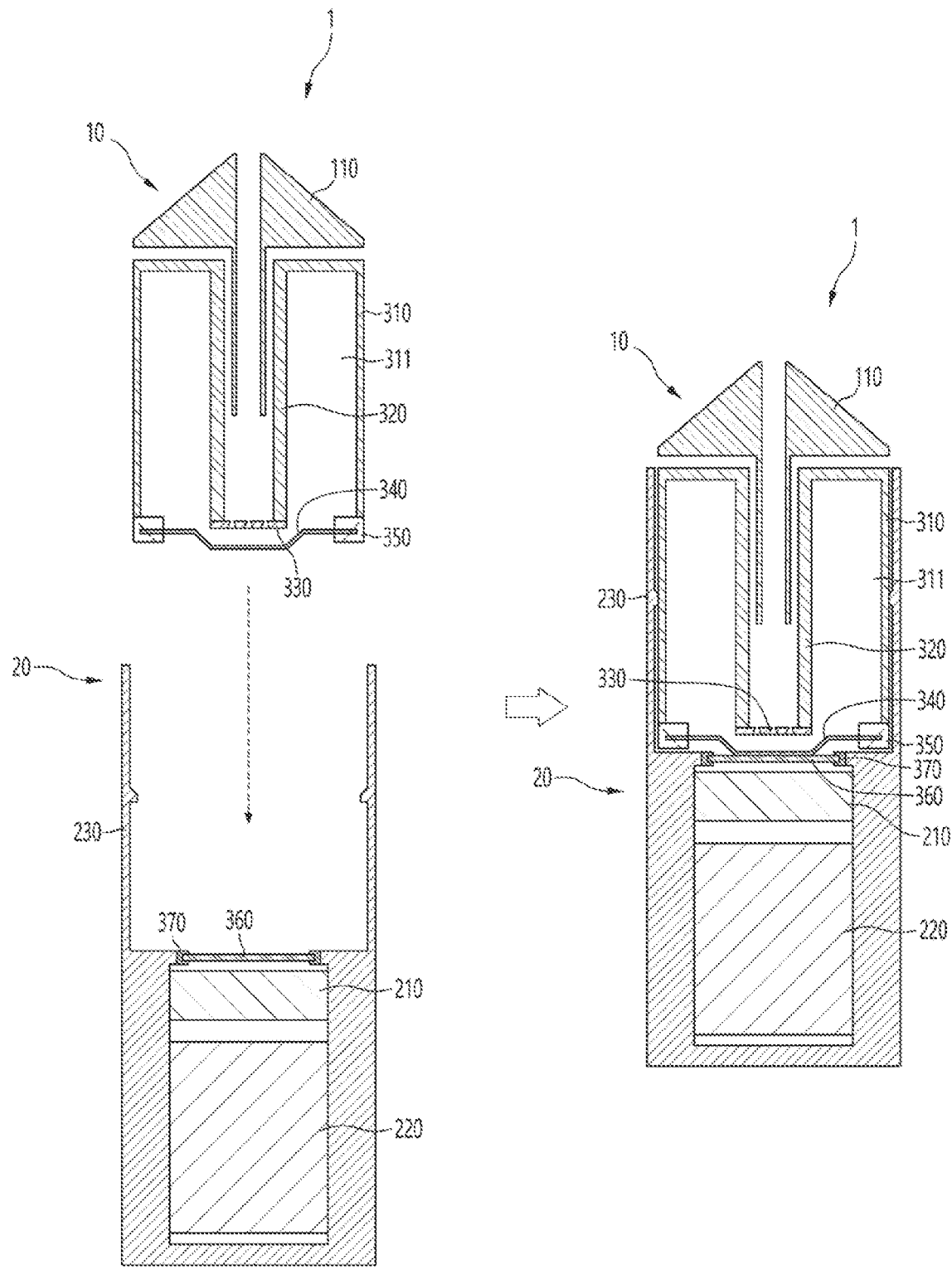

[FIG. 4]
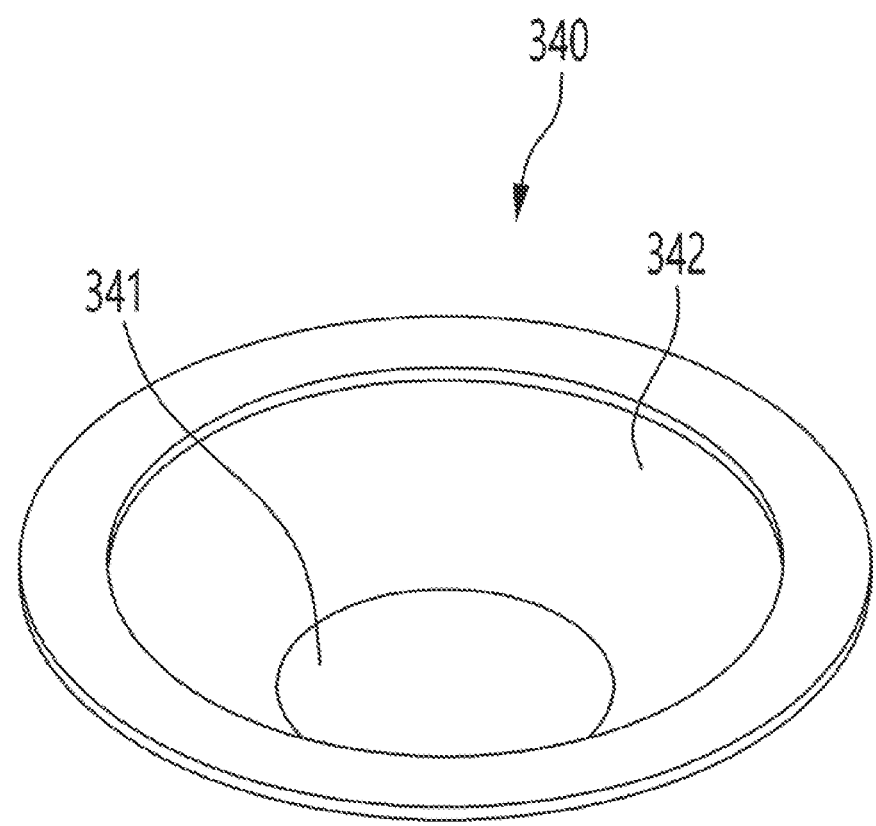

[FIG. 5]
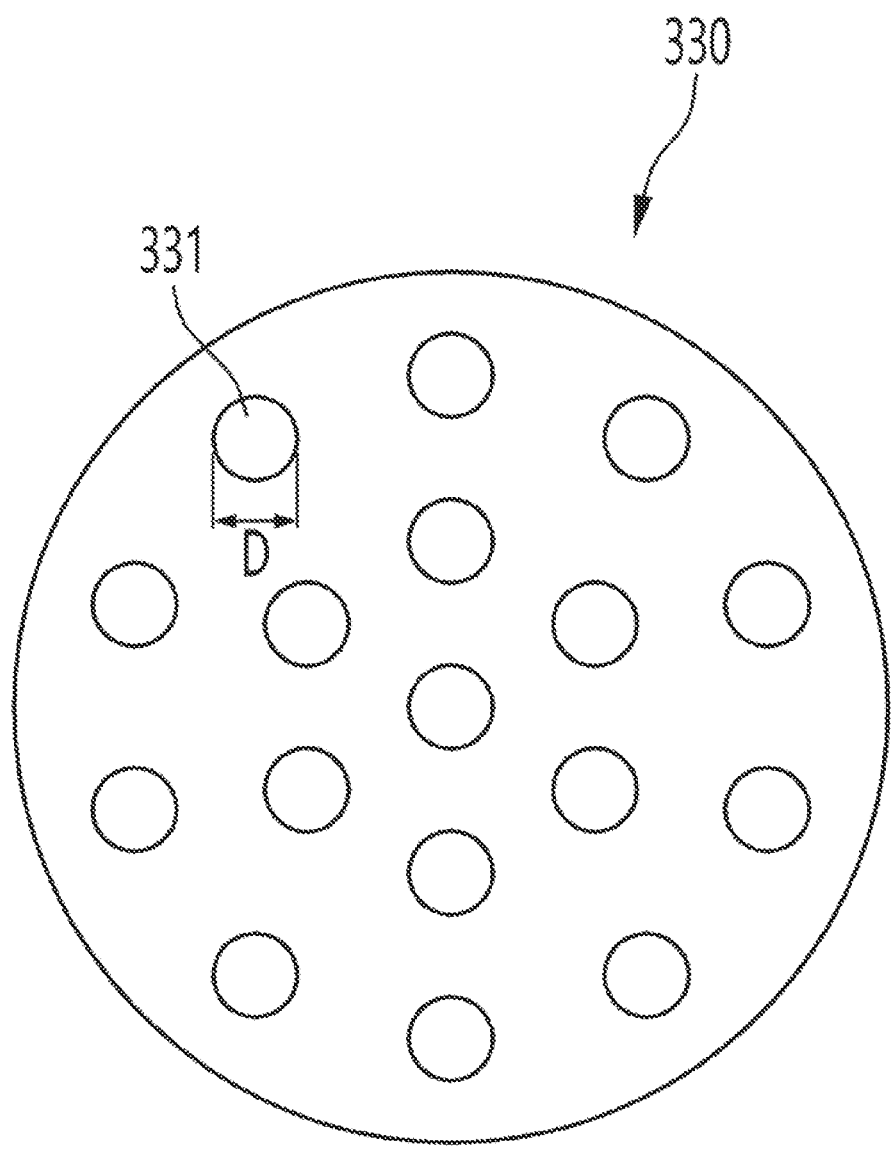

[FIG. 6]
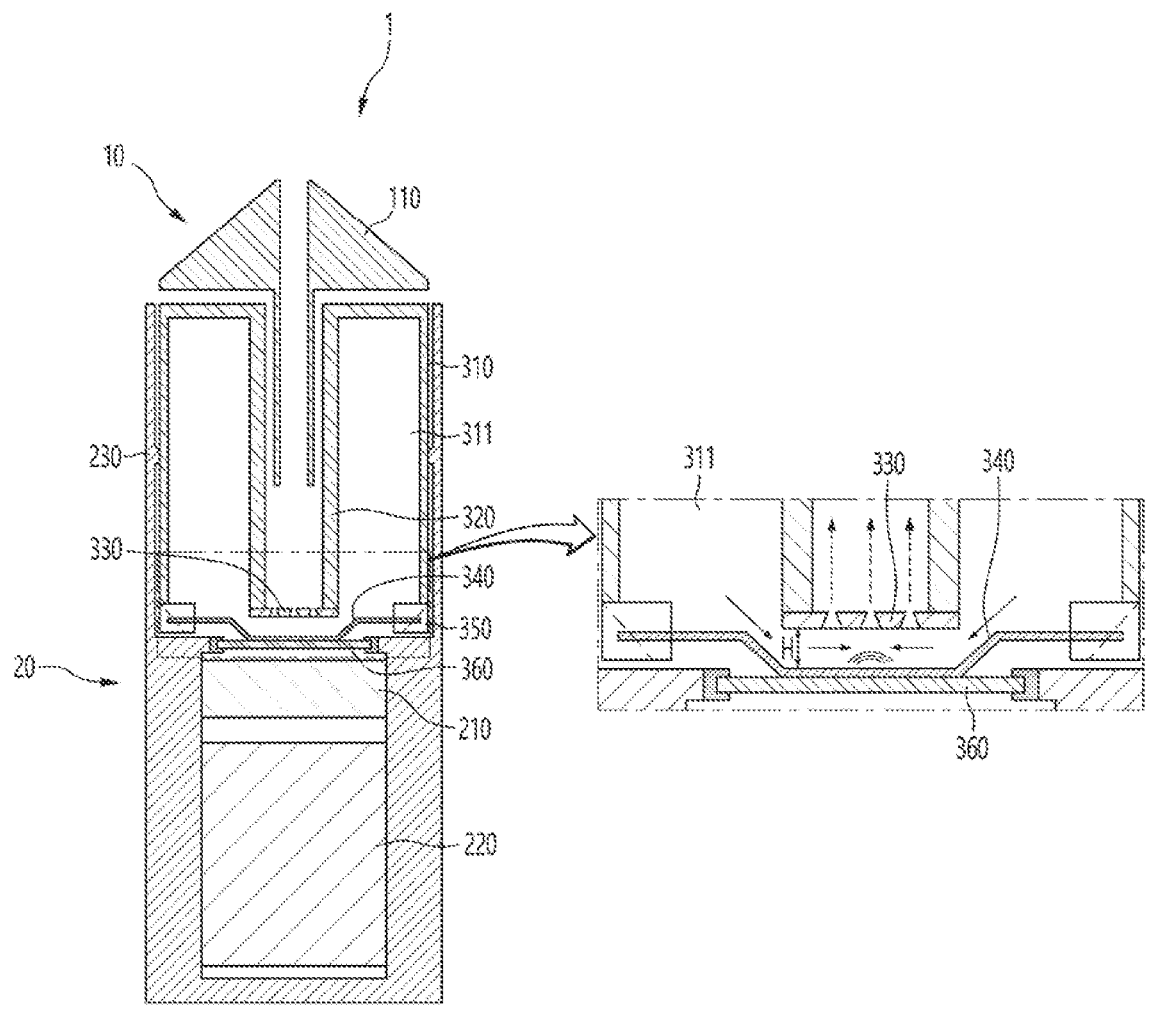

[FIG. 7]
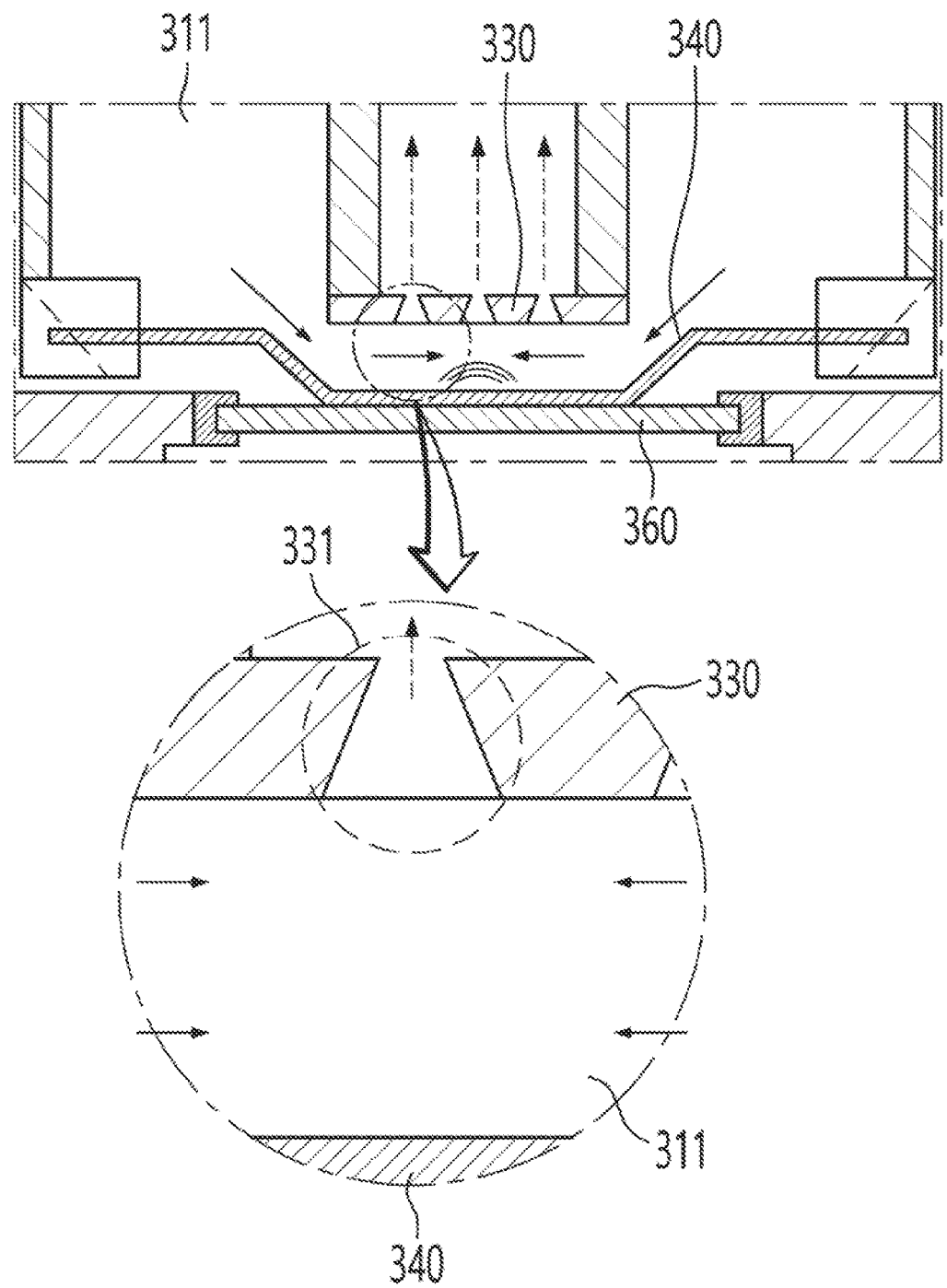

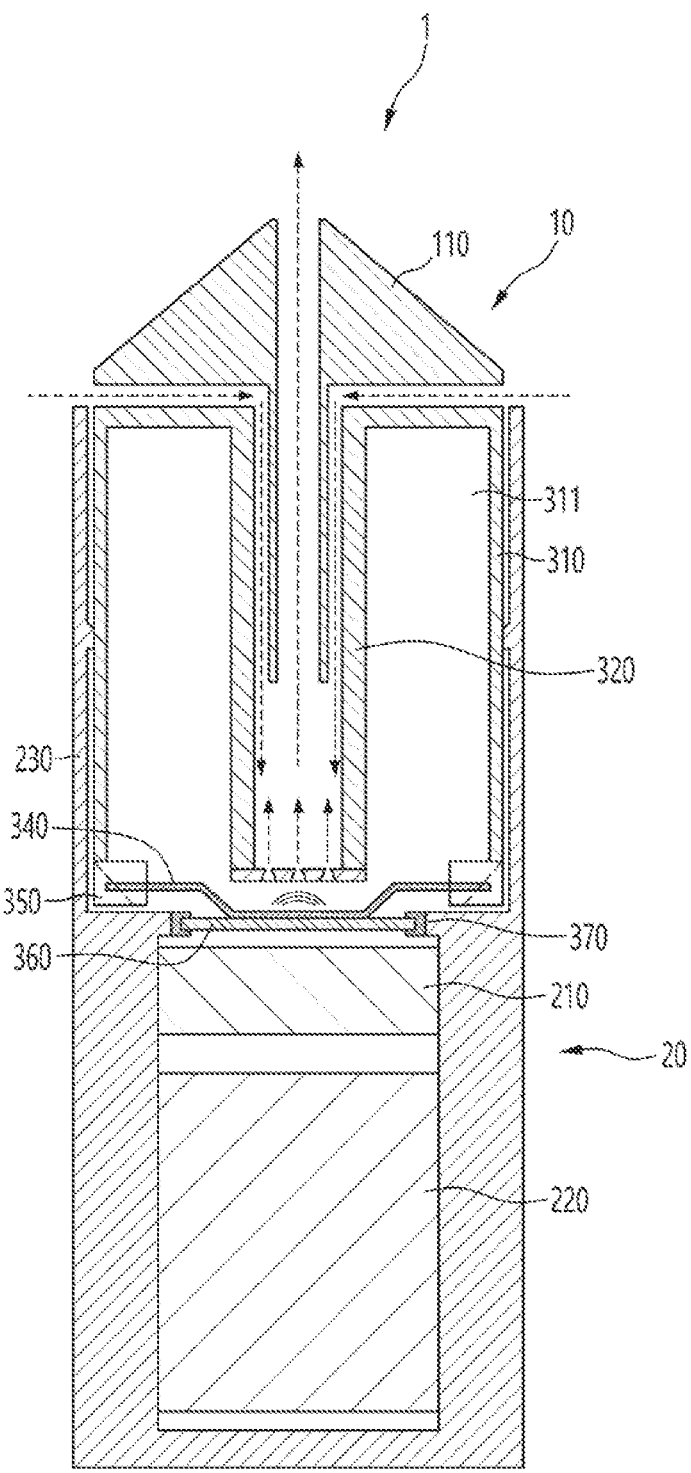
[FIG. 8]

[FIG. 9]
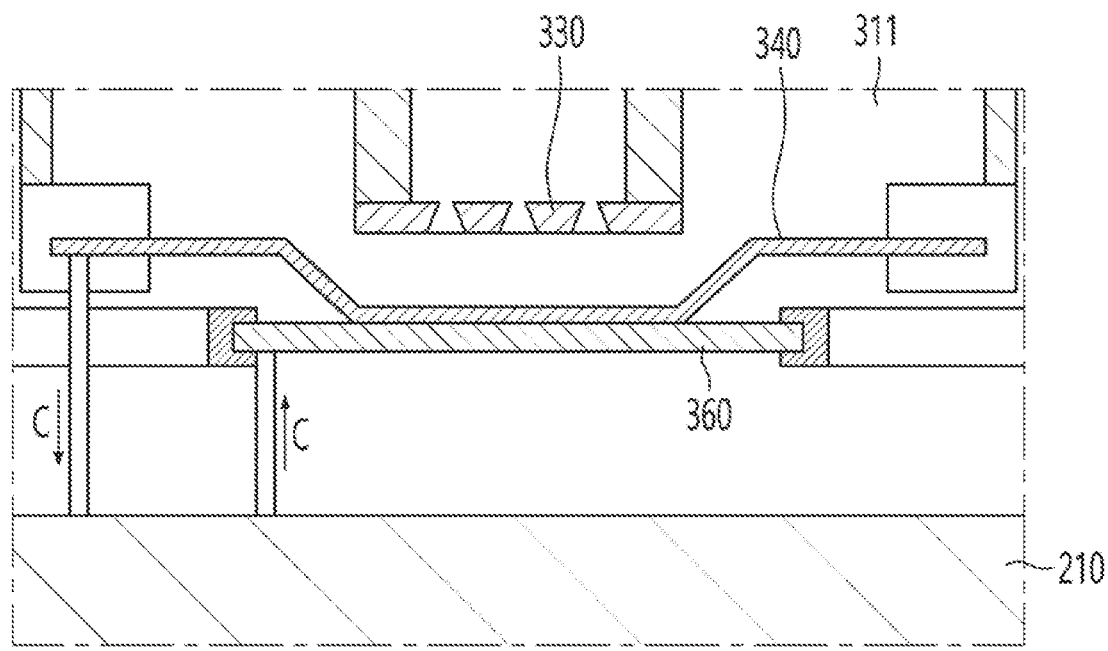

[FIG. 10]
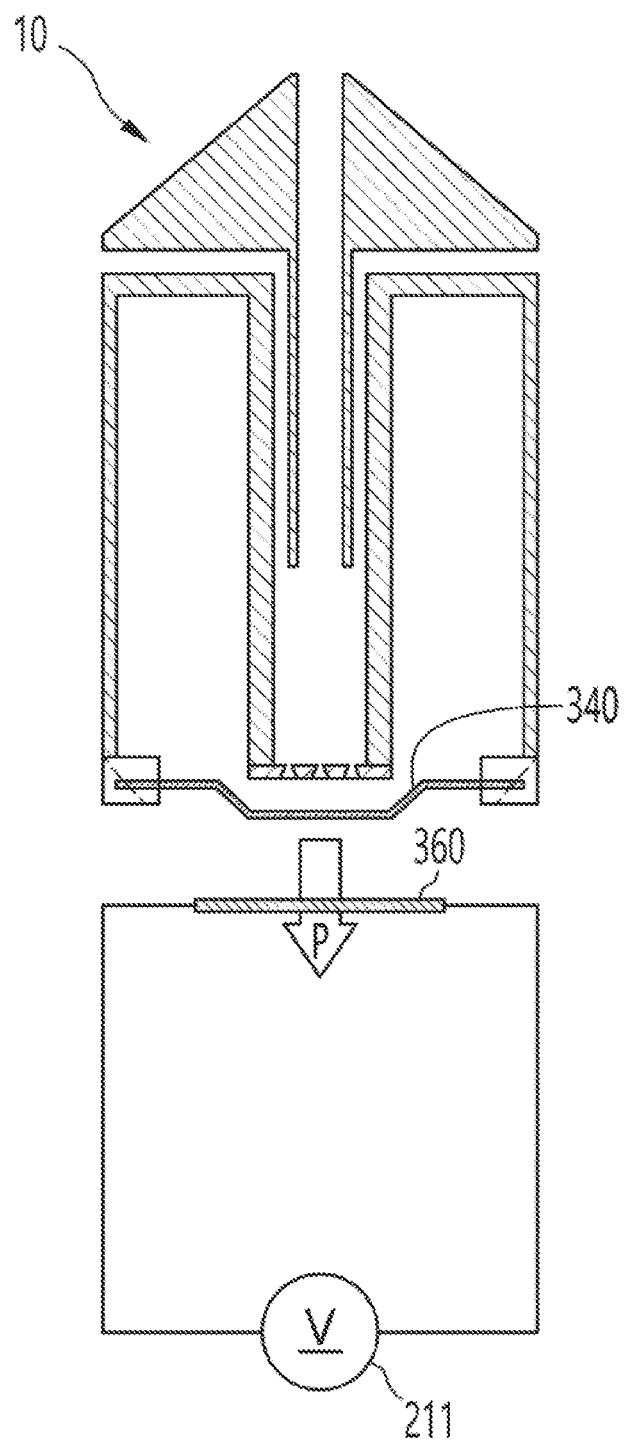

ULTRASONIC-BASED AEROSOL GENERATION DEVICE AND CARTRIDGE RECOGNITION METHOD THEREOF

CROSS REFERENCE TO RELATED APPLICATIONS

This application is a National Stage of International Application No. PCT/KR2021/008927 filed Jul. 13, 2021, claiming priority based on Korean Patent Application No. 10-2020-0107927 filed Aug. 26, 2020, the contents of all of which are incorporated herein by reference in their entirety.

TECHNICAL FIELD

The present disclosure relates to an ultrasonic-based aerosol generation device and a cartridge recognition method thereof, and more particularly, to an ultrasonic-based aerosol generation device, which is capable of reducing cartridge replacement costs and ensuring immediate aerosol generation, and a cartridge recognition method performed by the device.

BACKGROUND ART

In recent years, demand for alternative methods that overcome the disadvantages of general cigarettes has increased. For example, demand for devices (so-called liquid-type aerosol generation devices) that vaporize a liquid aerosol-forming substrate to generate an aerosol has increased. Recently, ultrasonic-based aerosol generation devices that generate an aerosol through ultrasonic vibrations have been proposed.

Most of the ultrasonic-based aerosol generation devices which have been proposed so far adopt a cartridge (or cartomizer) replacement structure in consideration of user convenience. Also, a replaceable cartridge basically consists of a liquid reservoir, a wick, and a vibrator. However, in such a structure, since the vibrator, which is a relatively expensive component, is included in the cartridge, there is a problem that a cartridge replacement cost (or cartridge unit cost) is increased.

Due to the cost problem, some of the ultrasonic-based aerosol generation devices adopt a method in which liquid is refilled without replacing a cartridge. However, the liquid refill method complicates the structure of the aerosol generation device and causes an inconvenience of a user having to refill the liquid. Further, in some cases, the user's clothes or body may be stained with the liquid during the liquid refill process, and this may cause considerable discomfort to the user.

Meanwhile, the ultrasonic-based aerosol generation devices that adopt the cartridge replacement structure generally include an additional sensor to recognize a state of insertion or coupling of a cartridge. However, the use of an additional sensor increases manufacturing costs of the aerosol generation devices and complicates an internal structure thereof.

DISCLOSURE

Technical Problem

Some embodiments of the present disclosure are directed to providing an ultrasonic-based aerosol generation device capable of reducing a cartridge replacement cost (or cartridge unit cost).

Some embodiments of the present disclosure are also directed to providing an ultrasonic-based aerosol generation device capable of ensuring immediate aerosol generation in response to puffs.

Some embodiments of the present disclosure are also directed to providing an ultrasonic-based aerosol generation device, which is capable of recognizing a coupling state of a cartridge without use of an additional sensor, and a cartridge recognition method performed by the device.

Objectives of the present disclosure are not limited to the above-mentioned objectives, and other unmentioned objectives should be clearly understood by those of ordinary skill in the art to which the present disclosure pertains from the description below.

Technical Solution

An ultrasonic-based aerosol generation device according to some embodiments of the present disclosure includes a liquid reservoir configured to store a liquid aerosol-forming substrate, a vibration element configured to provide ultrasonic vibrations to the stored liquid aerosol-forming substrate to form an aerosol, and a porous member disposed apart from the vibration element and including a plurality of holes. Here, the aerosol may be formed as the stored liquid aerosol-forming substrate passes through the plurality of holes due to the provided ultrasonic vibrations.

In some embodiments, the vibration element may include a vibration member configured to generate the ultrasonic vibrations and a vibration transmission member configured to transmit the generated ultrasonic vibration to the stored liquid aerosol-forming substrate. Here, the vibration transmission member may be included in a replaceable cartridge together with the liquid reservoir and the porous member, and the vibration member may be included in a control main body together with a controller configured to control the aerosol generation device.

In some embodiments, the vibration member and the vibration transmission member may each include a flat portion, and as the cartridge is coupled to the control main body, the flat portions of the vibration member and the vibration transmission member may come in close contact with each other.

In some embodiments, the vibration member and the vibration transmission member may be made of an electrical conductor, and the controller may, on the basis of whether electrical conduction occurs between the vibration member and the vibration transmission member, determine whether the vibration member and the vibration transmission member are in close contact.

In some embodiments, the vibration member may be implemented on the basis of a piezoelectric element, and the controller may, on the basis of a voltage generated in the vibration member, determine whether the vibration member and the vibration transmission member are in close contact.

In some embodiments, a thickness of at least a portion of the vibration transmission member may be in a range of 0.01 mm to 1 mm.

In some embodiments, a separation distance between the vibration element and the porous member may be in a range of 0.1 mm to 2 mm.

In some embodiments, a thickness of the porous member may be in a range of 0.01 mm to 2 mm.

In some embodiments, a size of the hole may be in a range of 1 μm to 500 μm.

In some embodiments, the hole may be formed in the shape of an orifice.

Advantageous Effects

According to some embodiments of the present disclosure, a vibration member, which is a relatively expensive component, can be disposed at a control main body side instead of being disposed in a cartridge. Accordingly, a cartridge replacement cost (or cartridge unit cost) can be significantly reduced.

Also, since the vibration member is excluded from the cartridge, a structure of the cartridge can be simplified. Accordingly, a defect occurrence rate can be significantly reduced during manufacture of the cartridge, and waterproof design and/or dustproof design thereof can also be facilitated.

In addition, a variation in vapor production due to a variation in the vibration member can be prevented. For example, in a case in which the vibration member is included in the cartridge, vapor production may not be consistent due to the vibration member being changed every time the cartridge is replaced. That is, the variation in the vibration member (e.g., variation in manufacture) may directly affect the aerosol generation device and cause vapor production to vary every time the cartridge is replaced. However, when the vibration member is disposed at the control main body side, since the vibration member is not replaced, uniformity of vapor production can be maintained.

In addition, a vibration transmission member can be disposed in the cartridge. The vibration transmission member can transmit vibrations, which are generated by the vibration member, to a liquid to allow an aerosol to be smoothly generated even when the vibration member is disposed at the control main body side.

In addition, as the cartridge is coupled to the control main body, the vibration transmission member and the vibration member may come in close contact with each other. Accordingly, the vibrations generated by the vibration member can be transmitted without loss to a liquid through the vibration transmission member, and thus aerosol generation can smoothly occur.

In addition, since a porous member including a plurality of holes is disposed at a position properly spaced apart from the vibration transmission member, it is possible to ensure immediate aerosol generation upon a puff. Specifically, as the vibrations transmitted by the vibration transmission member push a liquid present between the vibration transmission member and the porous member in a direction toward the porous member. Accordingly, the pushed liquid is rapidly vaporized by passing through the plurality of holes, and thus an aerosol can be generated immediately upon a puff.

In addition, whether the vibration member and the vibration transmission member are in close contact can be determined on the basis of whether electrical conduction occurs between the two members or using a piezoelectric phenomenon of the vibration member, and a coupling state of the cartridge can be recognized based on the determination. In other words, since the coupling state of the cartridge can be recognized without an additional cartridge recognition sensor, manufacturing costs of the aerosol generation device can be reduced, and an internal structure thereof can be further simplified.

The advantageous effects according to the technical spirit of the present disclosure are not limited to the above-mentioned advantageous effects, and other unmentioned advantageous effects should be clearly understood by those of ordinary skill in the art from the description below.

DESCRIPTION OF DRAWINGS

FIG. 1 is an exemplary view conceptually illustrating a structure of an ultrasonic-based aerosol generation device according to some embodiments of the present disclosure.

FIG. 2 is an exemplary view conceptually illustrating a structure of a vaporizer according to some embodiments of the present disclosure.

FIG. 3 is an exemplary view illustrating a detailed structure of the ultrasonic-based aerosol generation device according to some embodiments of the present disclosure.

FIG. 4 is an exemplary view illustrating a vibration transmission member according to some embodiments of the present disclosure.

FIGS. 5 to 7 are exemplary views illustrating a porous member according to some embodiments of the present disclosure.

FIG. 8 is an exemplary view illustrating an airflow path structure of the ultrasonic-based aerosol generation device according to some embodiments of the present disclosure.

FIG. 9 is an exemplary view illustrating a cartridge recognition method according to a first embodiment of the present disclosure.

FIG. 10 is an exemplary view illustrating a cartridge recognition method according to a second embodiment of the present disclosure.

MODES OF THE INVENTION

Hereinafter, exemplary embodiments of the present disclosure will be described in detail with reference to the accompanying drawings. Advantages and features of the present disclosure and methods of achieving the same should become clear with embodiments described in detail below with reference to the accompanying drawings. However, the technical spirit of the present disclosure is not limited to the following embodiments and may be implemented in various different forms. The embodiments make the technical spirit of the present disclosure complete and are provided to completely inform those of ordinary skill in the art to which the present disclosure pertains of the scope of the present disclosure. The technical spirit of the present disclosure is defined only by the scope of the claims.

In assigning reference numerals to components of each drawing, it should be noted that the same reference numerals are assigned to the same components as much as possible even when the components are illustrated in different drawings. Also, in describing the present disclosure, when detailed description of a known related configuration or function is deemed as having the possibility of obscuring the gist of the present disclosure, the detailed description thereof will be omitted.

Unless otherwise defined, all terms including technical or scientific terms used herein have the same meaning as commonly understood by those of ordinary skill in the art to which the present disclosure pertains. Terms defined in commonly used dictionaries should not be construed in an idealized or overly formal sense unless expressly so defined herein. Terms used herein are for describing the embodiments and are not intended to limit the present disclosure. In the following embodiments, a singular expression includes a plural expression unless the context clearly indicates otherwise.

Also, in describing components of the present disclosure, terms such as first, second, A, B, (a), and (b) may be used. Such terms are only used for distinguishing one component from another component, and the essence, order, sequence, or the like of the corresponding component is not limited by the terms. In a case in which a certain component is described as being "connected," "coupled," or "linked" to another component, it should be understood that, although the component may be directly connected or linked to the other component, still another component may also be "connected," "coupled," or "linked" between the two components.

The terms "comprises" and/or "comprising" used herein do not preclude the presence or addition of one or more components, steps, operations, and/or devices other than those mentioned.

Some terms used in various embodiments of the present disclosure will be clarified prior to description thereof.

In the following embodiments, "aerosol-forming substrate" may refer to a material that is able to form an aerosol. The aerosol may include a volatile compound. The aerosol-forming substrate may be a solid or liquid. For example, solid aerosol-forming substrates may include solid materials based on tobacco raw materials such as reconstituted tobacco leaves, shredded tobacco, and reconstituted tobacco, and liquid aerosol-forming substrates may include liquid compositions based on nicotine, tobacco extracts, and/or various flavoring agents. However, the scope of the present disclosure is not limited to the above-listed examples. In the following embodiments, "liquid" may refer to a liquid aerosol-forming substrate.

In the following embodiments, "aerosol generation device" may refer to a device that generates an aerosol using an aerosol-forming substrate in order to generate an aerosol that can be inhaled directly into the user's lungs through the user's mouth.

In the following embodiments, "puff" refers to inhalation by a user, and the inhalation may refer to a situation in which a user draws smoke into his or her oral cavity, nasal cavity, or lungs through the mouth or nose.

Hereinafter, various embodiments of the present disclosure will be described in detail with reference to the accompanying drawings.

FIG. 1 is an exemplary view conceptually illustrating a structure of an ultrasonic-based aerosol generation device 1 according to some embodiments of the present disclosure. In particular, FIG. 1 sequentially illustrates states before and after a cartridge 10 is mounted.

As illustrated in FIG. 1, the ultrasonic-based aerosol generation device 1 may include a cartridge 10 and a control main body 20. However, only the components relating to the embodiment of the present disclosure are illustrated in FIG. 1. Therefore, those of ordinary skill in the art to which the present disclosure pertains should understand that the ultrasonic-based aerosol generation device 1 may further include general-purpose components other than the components illustrated in FIG. 1. Hereinafter, each component of the aerosol generation device 1 will be described.

The cartridge 10 may refer to a container configured to store a liquid aerosol-forming substrate. Also, in some cases, the cartridge 10 may further include a mouthpiece and some or all of the components of a vaporizer (e.g., cartomizer). For example, as illustrated, the cartridge 10 may be configured to further include a mouthpiece 110 and some components of a vaporizer 30. As another example, the cartridge 10 may be configured to exclude the mouthpiece 110 and only further include some components of the vaporizer 30.

FIG. 1 illustrates an example in which the cartridge 10 is coupled to the control main body 20 to form an upper portion of the aerosol generation device 1 and the control main body 20 forms a lower portion of the aerosol generation device 1, but the scope of the present disclosure is not limited to such a structure. In some other embodiments, the cartridge 10 may be a component mounted in a housing of the aerosol generation device 1.

The cartridge 10 may be a replaceable component. That is, the cartridge 10 may be replaced with a new cartridge instead of being refilled with liquid when the liquid therein is used up. In this case, since the overall structure of the aerosol generation device 1 may be simplified, advantages in terms of manufacturing processes (e.g., reduction of manufacturing costs, reduction of defect rates, etc.) may be secured. Further, since the inconvenience of a user having to directly refill the cartridge with liquid is eliminated, the market competitiveness of the product may be improved. The cost of replacing the cartridge 10 may be a problem, but this problem may be addressed by excluding some components (that is, a vibration member which is relatively expensive) of the vaporizer 30 from the cartridge 10. Hereinafter, description will be continued assuming that the cartridge 10 is a replaceable component.

As conceptually illustrated in FIG. 1, the cartridge 10 according to an embodiment may include the mouthpiece 110 and some components of the vaporizer 30. More specifically, as illustrated in FIG. 2, the vaporizer 30 may include components such as a liquid reservoir configured to store a liquid aerosol-forming substrate 311, a vibration member 360 configured to vaporize a liquid through vibrations (ultrasonic vibrations), and an airflow tube 320 configured to deliver the vaporized liquid in a direction toward the mouthpiece 110. Among these components, the vibration member 360 may be disposed at the control main body 20 side (e.g., below the dotted line in FIG. 2), and the other components may be disposed at the cartridge 10 side (e.g., above the dotted line in FIG. 2). In this case, the vaporizer 30 may be configured as the cartridge 10 and the control main body 20 are coupled to each other, and since the vibration member, which is a relatively expensive component, is excluded from the cartridge 10, the replacement cost (or unit cost) of the cartridge 10 may be significantly reduced. The structure of the cartridge 10 will be described in more detail below with reference to FIG. 3 and so on.

In some embodiments, as illustrated in FIG. 2, the vaporizer 30 may further include a vibration transmission member 340 disposed at the cartridge 10 side. That is, the vaporizer 30 may include the vibration transmission member 340 and the vibration member 360 as vibration elements. The vibration transmission member 340 may transmit vibrations, which are generated by the vibration member 360 at the control main body 20 side, to the liquid 311 to smoothly generate an aerosol. The vibration transmission member 340 will be described in more detail below with reference to FIG. 3 and so on.

The description of the components of the aerosol generation device 1 will be continued by referring back to FIG. 1.

The control main body 20 may perform an overall control function for the aerosol generation device 1. As illustrated, the control main body 20 may be coupled to the cartridge 10. In a case in which the cartridge 10 is a component embedded in the aerosol generation device 1, the control main body 20 may be coupled to an upper housing that includes the cartridge 10.

As illustrated, the control main body 20 may include a controller 210 and a battery 220. Also, as mentioned above, the control main body 20 may further include the vibration member 360 and the like. Components of the control main body 20 other than the controller 210 and the battery 220 will be described below with reference to FIG. 3, and hereinafter, the controller 210 and the battery 220 will be briefly described.

The controller 210 may control the overall operation of the aerosol generation device 1. For example, the controller 210 may control the operation of the vaporizer 30 and the battery 220 and also control the operation of other components included in the aerosol generation device 1. The controller 210 may control the power supplied by the battery 220 and the vibration frequency, vibration intensity, or the like of the vibration member 360. In a case in which the aerosol generation device 1 further includes a heater (not illustrated), the controller 210 may also control a heating temperature of the heater (not illustrated).

Also, the controller 210 may check a state of each of the components of the aerosol generation device 1 and determine whether the aerosol generation device 1 is in an operable state.

In some embodiments, the controller 210 may determine whether the vibration transmission member 340 and the vibration member 360 are in close contact and may, on the basis of a determined result, recognize a coupling state of the cartridge 10 (e.g., whether the cartridge 10 is coupled, a degree of coupling of the cartridge 10, etc.). For example, the controller 210 may determine whether the vibration transmission member 340 and the vibration member 360 are in close contact on the basis of whether electrical conduction occurs therebetween or may determine whether the vibration transmission member 340 and the vibration member 360 are in close contact by using a piezoelectric phenomenon of the vibration member 360. Also, the controller 210 may, on the basis of a determined result, recognize a coupling state of the cartridge 10 without a separate sensor. According to the present embodiment, since an additional sensor is not necessary for recognizing a coupling state of the cartridge 10, manufacturing costs of the aerosol generation device 1 may be reduced, and complexity of an internal structure of the aerosol generation device 1 may be reduced. The present embodiment will be described in detail below with reference to FIGS. 9 and 10.

The controller 210 may be implemented with at least one processor. The processor may also be implemented with an array of a plurality of logic gates or implemented with a combination of a general-purpose microprocessor and a memory which stores a program that may be executed by the microprocessor. Also, those of ordinary skill in the art to which the present disclosure pertains should clearly understand that the controller 210 may also be implemented with other forms of hardware.

Next, the battery 220 may supply the power used to operate the aerosol generation device 1. For example, the battery 220 may supply power to allow the vibration member 360, which constitutes the vaporizer 30, to generate vibrations or may supply power required for the controller 210 to operate.

Also, the battery 220 may supply power required to operate electrical components such as a display (not illustrated), a sensor (not illustrated), and a motor (not illustrated) which are installed in the aerosol generation device 1.

The structure of the control main body 20 will be described in more detail below with reference to FIG. 3 and so on.

The ultrasonic-based aerosol generation device 1 according to some embodiments of the present disclosure has been schematically described above with reference to FIGS. 1 and 2. According to the above description, the vibration member 360, which is a relatively expensive component, may be disposed at the control main body 20 side instead of being disposed in the cartridge 10. Accordingly, a cartridge replacement cost (or cartridge unit cost) may be significantly reduced. Also, since the vibration member 360 is excluded from the cartridge 10, the structure of the cartridge 10 may be simplified, a defect occurrence rate may be significantly reduced during manufacture of the cartridge, and waterproof design and/or dustproof design thereof may also be facilitated. In addition, an occurrence of a variation in vapor production due to a variation in the vibration member 360 (e.g., variation in manufacture) may be prevented. For example, in a case in which the vibration member 360 is included in the cartridge 10, a variation in vapor production may occur due to the vibration member 360 being changed every time the cartridge 10 is replaced. However, when the vibration member 360 is disposed at the control main body 20 side, since the same vibration member 360 is continuously used, uniformity of vapor production may be maintained.

Hereinafter, the structure and operation principle of the ultrasonic-based aerosol generation device 1 will be described in more detail with reference to FIG. 3 and so on.

FIG. 3 is an exemplary view illustrating a detailed structure of the ultrasonic-based aerosol generation device 1 according to some embodiments of the present disclosure. In particular, FIG. 3 sequentially illustrates states before and after the cartridge 10 is mounted.

As illustrated in FIG. 3, the cartridge 10 may include a cartridge housing, the mouthpiece 110, a liquid reservoir 310, the vibration transmission member 340, a porous member 330, and the airflow tube 320. However, only the components relating to the embodiment of the present disclosure are illustrated in FIG. 3. Therefore, those of ordinary skill in the art to which the present disclosure pertains should understand that the cartridge 10 may further include general-purpose components other than the components illustrated in FIG. 3. Hereinafter, each component of the cartridge 10 will be described.

The cartridge housing may form an exterior of the cartridge 10. FIG. 3 illustrates the cartridge housing as not being distinct from an outer wall of the liquid reservoir 310, but a portion of the cartridge housing may or may not constitute the outer wall of the liquid reservoir 310. A portion of the cartridge housing may also serve as the mouthpiece 110, or a separate mouthpiece structure may be designed to be mounted in the cartridge housing. The cartridge housing may be made of a suitable material to protect the components inside the cartridge 10.

Also, the cartridge housing may form an open lower end portion. The vibration transmission member 340 may be disposed in the vicinity of the open lower end portion. In this way, as illustrated, the vibration transmission member 340 may come in close contact with the vibration member 360 as the cartridge 10 is coupled to the control main body 20. That is, when the cartridge 10 is mounted, it is possible to form a structure in which the vibration transmission member 340 and the vibration member 360 come in close contact with each other, and such a structure may maximize a vibration transmission area and minimize loss during vibration transmission, thus ensuring prompt aerosol generation and sufficient vapor production.

Next, the mouthpiece 110 may be disposed at one end of the aerosol generation device 1 or cartridge 10 and may come in contact with the oral region of the user to allow inhalation of the aerosol generated in the cartridge 10. In other words, when the user holds the mouthpiece 110 in his or her mouth and inhales, the aerosol generated in the cartridge 10 may be delivered to the user through the mouthpiece 110.

Next, the liquid reservoir 310 may store the liquid aerosol-forming substrate 311. The liquid reservoir 310 may include a single storage space or a plurality of storage spaces. For example, the liquid reservoir 310 may include a plurality of storage spaces to separately store aerosol-forming substrates having different components or composition ratios.

Next, the vibration transmission member 340 may transmit the vibrations generated by the vibration member 360 to the liquid 311. For example, the vibration transmission member 340 may transmit the vibrations generated by the vibration member 360 to the liquid 311 disposed nearby to vaporize the liquid 311. The vibration transmission member 340 may also serve to prevent the liquid 311 from leaking in a downward direction (that is, a direction toward the control main body 20).

The vibration transmission member 340 may be disposed in the vicinity of the open lower end portion of the cartridge 10 and may include a flat portion and have a shape that protrudes downward. For example, as illustrated in FIGS. 3 and 4, the vibration transmission member 340 may include a flat lower surface 341 and an inclined surface 342 that allows the lower surface 341 to protrude downward. In this case, the flat lower surface 341 may easily come in close contact with the vibration member 360 as the cartridge 10 is coupled to the control main body 20.

The vibration transmission member 340 may be made of a material that facilitates vibration transmission and/or formed in a shape that facilitates vibration transmission. Specific materials and/or shapes thereof may vary according to an embodiment.

In some embodiments, a thickness of at least a portion (e.g., the lower surface) of the vibration transmission member 340 may be in a range of about 0.01 mm to 1 mm, preferably, in a range of about 0.02 mm to 0.7 mm or about 0.03 mm to 0.5 mm, and more preferably, in a range of about 0.03 mm to 0.1 mm, about 0.03 mm to 0.2 mm, about 0.03 mm to 0.3 mm, or about 0.03 mm to 0.4 mm. Within such numerical ranges, loss may be minimized during vibration transmission, and suitable durability may also be secured. For example, in a case in which the thickness of the vibration transmission member 340 is too thick, vibrations may be absorbed by the vibration transmission member 340. On the other hand, in a case in which the thickness of the vibration transmission member 340 is too thin, suitable durability cannot be secured and thus the vibration transmission member 340 may be easily damaged.

Also, in some embodiments, the vibration transmission member 340 may be made of a material having suitable strength (e.g., a hard material) such as a metal. For example, the vibration transmission member 340 may be made of a metal material such as stainless steel and aluminum. In this case, the absorption of vibrations by the vibration transmission member 340 may be minimized, and material deformation due to contact with the liquid 311 may also be minimized.

Also, in some embodiments, the vibration transmission member 340 may include a flat lower surface (e.g., 341) and an inclined surface (e.g., 342) that allows the lower surface (e.g., 341) to protrude downward (see FIG. 3 or 4), and an angle between the inclined surface (e.g., 342) and a direction perpendicular to the lower surface (that is, a direction in which the cartridge 10 is inserted) may be in a range of about 15° to 70°. Preferably, the angle may be in a range of about 20° to 60°, about 25° to 55°, or about 30° to 50°. Within such numerical ranges, a close contact area between the lower surface (e.g., 341) and the vibration member 360 may be sufficiently secured, vibration transmission may be concentrated toward the airflow tube 320 due to the angle of the inclined surface (e.g., 342) and thus a vaporization rate may be increased, and vapor production may also be enhanced.

Next, the porous member 330 may be disposed to be spaced apart from the vibration transmission member 340 and serve to ensure immediate aerosol generation. For example, as illustrated, the porous member 330 may be spaced apart from the vibration transmission member 340 and disposed in the vicinity of a lower end portion of the airflow tube 320 (that is, in the vicinity of an inlet of the airflow tube). Here, the porous member 330 may refer to a member including a plurality of holes 331 as illustrated in FIG. 5. Examples of the porous member 330 may include a perforated member (e.g., a perforated plate), a mesh member (e.g., a mesh plate), and the like, but are not limited thereto. To provide more convenience in understanding, a vaporization mechanism using the vibration transmission member 340 and the porous member 330 will be briefly described with reference to FIG. 6.

As illustrated in FIG. 6, the liquid 311 may enter a space between the airflow tube 320 (or the porous member 330) and the vibration transmission member 340 (refer to the arrows). The liquid 311 may smoothly enter the space between the vibration transmission member 340 and the porous member 330 due to factors such as the capillary action, a change in a gap between the vibration transmission member 340 and the porous member 330 due to vibration, and a pressure difference due to vaporization of the liquid 311. The entering liquid 311 may be pushed in a direction toward the porous member 330 due to vibration of the vibration transmission member 340, and vaporization may occur as the pushed liquid 311 passes through the plurality of holes 331 formed in the porous member 330. As compared to a method in which the liquid 311 is directly vaporized through ultrasonic vibrations, this vaporization mechanism may ensure immediate aerosol generation. That is, since an aerosol may be generated without delay upon a puff, a user's smoking satisfaction may be improved.

For example, the porous member 330 may be made of materials such as plastics, metals (e.g., stainless steel), and silicones. However, the present disclosure is not limited thereto.

Also, the shape of the porous member 330 and the size, shape, and/or separation distance of the holes 331 may be designed in various ways according to an embodiment.

In some embodiments, the size of the holes 331 (e.g., a diameter D in FIG. 5) may be in a range of about 1 μm to 500 μm, and preferably, in a range of about 1 μm to 400 μm, 1 μm to 300 μm, 1 μm to 200 μm, or 1 μm to 100 μm. The size of the holes 331 is related to a particle size of an aerosol, and within the above numerical ranges, an aerosol having a suitable particle size may be generated, and sufficient vapor production may be ensured. For example, when the size of the holes 331 is too small, an aerosol may be generated in the form of very small particles that are not visible, and thus vapor production may be noticeably reduced. Also, vaporization may not be performed well, and thus the amount of generated aerosol itself may also decrease.

In some embodiments, the hole 331 may be formed in the shape of an orifice. For example, as illustrated in FIG. 7, the hole 331 may be formed in the shape of an orifice (e.g., having a trapezoidal longitudinal cross-section) in which a cross-sectional area tends to decrease in a direction in which an aerosol is delivered (that is, an upward direction). In this case, due to the orifice effect, a vaporization rate may be further improved, and aerosol particles may be generated to be smaller. However, the scope of the present disclosure is not limited to this example, and the hole 331 may also be formed in other shapes such as a cylindrical shape.

In some embodiments, the separation distance between the vibration transmission member 340 and the porous member 330 (e.g., a distance H in FIG. 6) may be in a range of about 0.1 mm to 2.0 mm, and preferably, in a range of about 0.1 mm to 1.8 mm, about 0.1 mm to 1.5 mm, about 0.2 mm to 1.2 mm, or about 0.3 mm to 1.0 mm. Within such numerical ranges, transfer of the liquid 311 and aerosol generation may smoothly occur. For example, when the separation distance is too large, vibrations transmitted by the vibration transmission member 340 may be absorbed into the liquid 311, and vapor production may be reduced. Conversely, when the separation distance is too small, the transfer of the liquid 311 between the vibration transmission member 340 and the porous member 330 may not smoothly occur, and accordingly, vapor production may be reduced.

In some embodiments, the porous member 330 may be formed in a flat shape (e.g., plate shape) and have a thickness in a range of about 0.01 mm to 5 mm. Preferably, the thickness may be in a range of about 0.02 mm to 3 mm or about 0.03 mm to 2 mm. Within such numerical ranges, aerosol generation may smoothly occur, the vaporization rate may be improved, and suitable durability may be secured. For example, in a case in which the porous member 330 has a suitable small thickness like the above-listed values, the porous member 330 may also vibrate due to the transmitted vibrations such that vaporization is accelerated, and a phenomenon in which a condensed aerosol is adhered to the hole 331 and blocks the hole 331 may be prevented. Thus, aerosol generation may more smoothly occur.

Meanwhile, in some embodiments, as illustrated in FIG. 3, the cartridge 10 may further include a fixing member 350 configured to fix an edge of the vibration transmission member 340. The fixing member 350 may fix an edge of the vibration transmission member 340 to allow a central portion (that is, a flat portion) of the vibration transmission member 340 to transmit vibrations well. Accordingly, the vaporization rate may be increased, and vapor production may be further enhanced. In addition, the fixing member 350 may serve to absorb vibrations of the vibration transmission member 340 so that the vibrations are not transmitted to the outside of the aerosol generation device 1. Therefore, preferably, the fixing member 350 may be made of a material, such as a silicone material, that is able to absorb vibrations and is hardly changed physically and chemically (e.g., a material which is not changed physically and chemically upon contact with a liquid). Also, the fixing member 350 may seal a gap between the vibration transmission member 340 and the cartridge housing to prevent the liquid 311 or aerosol from leaking downward.

A specific shape of the fixing member 350 and/or the number of fixing members 350 may be designed in various ways. For example, the fixing member 350 may be designed as a single ring that extends along a periphery of the vibration transmission member 340, or a plurality of fixing members 350 may be designed to fix the edge of the vibration transmission member 340.

Meanwhile, in some embodiments, the cartridge 10 may further include a heater (not illustrated). The heater may be disposed around the vibration transmission member 340 or porous member 330 to heat the liquid 311 so that vaporization by vibration is accelerated. The heater may operate as an auxiliary component to assist vaporization of the liquid 311. For example, since the aerosol-forming substrate 311 is a viscous liquid, it may be difficult to obtain satisfactory vaporization performance just by ultrasonic vibrations, and in this case, the vaporization performance of the aerosol generation device 1 may be improved through the heater (not illustrated). A heating temperature of the heater may be set to be much lower than a temperature of a heater of a typical heating-type aerosol generation device, and thus an increase in power consumption may be insignificant. The heater may be controlled by the controller 210 using various control methods.

For example, the controller 210 may increase the heating temperature of the heater every time a puff by the user is detected. Puff detection may be performed through an airflow sensor, but the scope of the present disclosure is not limited thereto.

As another example, the controller 210 may maintain the heating temperature of the heater during smoking regardless of whether a puff by the user occurs. In this way, during smoking, the liquid 311 may maintain a state in which it is easily vaporized.

As still another example, the controller 210 may determine the heating temperature of the heater in response to a user input. For example, if the user selects a high vapor production level, the controller 210 may increase the heating temperature of the heater, and in the opposite case, the controller 210 may decrease the heating temperature of the heater. In this way, vapor production may be provided according to the user's preferences, and thus the user's smoking satisfaction may be improved.

As yet another example, the controller 210 may analyze the user's puff pattern to determine the heating temperature of the heater. Here, the puff pattern may be defined on the basis of a puff length, a puff intensity, a puff interval, or the like, but is not limited thereto. As a specific example, in a case in which the puff length or puff intensity is increased or the puff interval is shortened, the controller 210 may increase the heating temperature of the heater. This is because longer or stronger inhalation by the user during smoking is highly likely to mean that the user is not satisfied with vapor production. In the opposite case, the controller 210 may decrease the heating temperature of the heater. Also, in a case in which the puff interval, puff length, or puff intensity is constantly maintained, the controller 210 may maintain the heating temperature of the heater.

As yet another example, the controller 210 may control the heater on the basis of various combinations of the examples described above.

The description of the components of the control main body 20 will be continued by referring back to FIG. 3.

As illustrated in FIG. 3, the control main body 20 may include a main body housing 230, the vibration member 360, the controller 210, and the battery 220. However, only the components relating to the embodiment of the present disclosure are illustrated in FIG. 3. Therefore, those of ordinary skill in the art to which the present disclosure pertains should understand that the control main body 20 may further include general-purpose components other than the components illustrated in FIG. 3. Hereinafter, each component of the control main body 20 will be described.

The main body housing 230 may form an exterior of the control main body 20. In some cases, the main body housing 230 may form an exterior of the aerosol generation device 1. The main body housing 230 may be made of a suitable material to protect the components inside the control main body 20. FIG. 3 illustrates an example in which the main body housing 230 forms a space in which the cartridge 10 may be inserted (mounted). However, the scope of the present disclosure is not limited thereto, and the cartridge 10 and the control main body 20 may also be coupled in other ways.

The descriptions of the controller 210 and the battery 220 will be omitted to avoid repeated description. Refer to the above descriptions relating to FIG. 1 for the descriptions of the controller 210 and the battery 220.

Next, the vibration member 360 may generate vibrations (ultrasonic vibrations) to vaporize the liquid aerosol-forming substrate 311. For example, the vibration member 360 may be implemented as a piezoelectric element capable of converting electrical energy into mechanical energy and may generate vibrations according to control of the controller 210. Since those of ordinary skill in the art should clearly understand the operation principle of the piezoelectric element, further description thereof will be omitted. The vibration member 360 may be electrically connected to the controller 210 and the battery 220.

In some embodiments, the vibration member 360 may include a flat portion (e.g., a plate shape), and as the cartridge 10 is coupled to the vibration member 360, the flat portions of the vibration member 360 and the vibration transmission member 340 may come in close contact with each other (refer to the right side in FIG. 3). In such a coupling structure, a vibration transmission area may be maximized, vibration loss may be minimized, and vapor production may be enhanced. Also, since the vibration member 360 is disposed in an open form (e.g., is open in the upward direction) at a portion where the vibration member 360 is coupled to the cartridge 10, the vibration member 360 may come in close contact with the vibration transmission member 340 as the cartridge 10 is coupled to the vibration member 360. In this case, not only is it convenient and easy to clean the vibration member 360, but also it is easy for the vibration member 360 to come in close contact with the vibration transmission member 340 when the cartridge 10 is mounted. In some embodiments, a coupling gel may be applied between the vibration member 360 and the vibration transmission member 340. In this case, ultrasonic vibrations may be transmitted without further loss to the liquid 311 through the vibration transmission member 340.

Also, in some embodiments, a vibration frequency of the vibration member 360 may be in a range of about 20 kHz to 1,500 kHz, in a range of about 50 kHz to 1,000 kHz, or in a range of about 100 kHz to 500 kHz. Within such numerical ranges, an appropriate vaporization rate and vapor production may be ensured. However, the present disclosure is not limited thereto.

Meanwhile, in some embodiments, as illustrated in FIG. 3, the control main body 20 may further include a fixing member 370 disposed to fix an edge of the vibration member 360. The fixing member 370 may serve to protect the vibration member 360 and absorb vibrations so that vibrations generated by the vibration member 360 are not transmitted to the outside of the main body housing 230. Therefore, preferably, the fixing member 370 may be made of a material, such as a silicone material, that is able to absorb vibrations. Also, the fixing member 370 may be made of a material that is waterproof or moisture-proof to seal a gap between the vibration member 360 and the main body housing 230. In this case, it is possible to significantly reduce a failure that occurs in the control main body 20 due to a liquid (e.g., the liquid 311) or a gas (e.g., an aerosol) leaking through the gap between the main body housing 230 and the vibration member 360. For example, damage to the control main body 20 or a failure thereof due to moisture may be prevented.

A specific shape of the fixing member 370 and/or the number of fixing members 370 may be designed in various ways. For example, the fixing member 370 may be designed as a single ring that extends along a periphery of the vibration member 360, or a plurality of fixing members 370 may be designed to fix the edge of the vibration member 360.

Hereinafter, an airflow path structure of the ultrasonic-based aerosol generation device 1 will be described with reference to FIG. 8.

FIG. 8 is an exemplary view illustrating an airflow path structure of the ultrasonic-based aerosol generation device 1 according to some embodiments of the present disclosure. FIG. 8 also illustrates flows of air (e.g., outside air, an aerosol), which are generated when a puff occurs, using arrows of different directions.

FIG. 8 illustrates an airflow path through which outside air (see dotted arrows) enters from one side surface or both side surfaces of the aerosol generation device 1 to the vicinity of a lower portion of the airflow tube 320 where the porous member 330 is disposed. The introduced outside air may pass through the porous member 330 and be mixed with a vaporized aerosol. Due to puffs, the mixed outside air and aerosol may be moved in a direction toward the mouthpiece 110 along an airflow path inside the airflow tube 320. In such an airflow path structure, the outside air and vaporized aerosol may be appropriately mixed in the airflow tube 320, and thus a high-quality aerosol may be formed.

The detailed structure and operation principle of the ultrasonic-based aerosol generation device 1 according to some embodiments of the present disclosure have been described above with reference to FIGS. 3 to 8. According to the above description, the vibration transmission member 340 disposed at the cartridge 10 side may transmit the vibrations generated by the vibration member 360 to the liquid 311 in order to allow an aerosol to be smoothly generated even when the vibration member 360 is disposed at the control main body 20 side. Also, as the cartridge 10 is coupled to the control main body 20, the vibration transmission member 340 and the vibration member 360 may form a structure in which the vibration transmission member 340 and the vibration member 360 come in close contact with each other. Accordingly, since the vibrations generated by the vibration member 360 may be transmitted without loss to the liquid 311 through the vibration transmission member 340, a vaporization rate and vapor production may be improved. Also, since the porous member 330 including a plurality of holes is disposed at a position properly spaced apart from the vibration transmission member 340, it is possible to ensure immediate aerosol generation upon a puff.

Meanwhile, the aerosol generation device 1 has been described above as including the vibration transmission member 340 and the vibration member 360 as the vibration elements. However, in some other embodiments of the present disclosure, the aerosol generation device 1 may only include the vibration member 360, which is disposed in the cartridge 10, as the vibration element. Even in this case, immediate aerosol generation may be ensured through the porous member 330 disposed to be spaced apart from the vibration member 360.

Hereinafter, a cartridge recognition method of the ultrasonic-based aerosol generation device 1 will be described with reference to FIGS. 9 and 10. The cartridge recognition method, which will be described below, may be performed by the controller 210 of the aerosol generation device 1. Therefore, in the following description, when the subject of a specific operation is omitted, the specific operation should be understood as being performed by the controller 210.

FIG. 9 is an exemplary view illustrating a cartridge recognition method according to a first embodiment of the present disclosure. Hereinafter, description will be given with reference to FIG. 9.

In the present embodiment, the vibration transmission member 340 and the vibration member 360 may be made of an electrical conductor. Also, each of the vibration transmission member 340 and the vibration member 360 may be electrically connected to the controller 210. For example, the vibration transmission member 340 may be electrically connected to the controller 210 as the cartridge 10 is coupled to the control main body 20.

Then, the controller 210 may determine whether the vibration transmission member 340 and the vibration member 360 are in close contact on the basis of whether electrical conduction occurs between the vibration transmission member 340 and the vibration member 360. Specifically, as illustrated, the controller 210 may determine whether the vibration transmission member 340 and the vibration member 360 are in close contact by applying a predetermined test current C to the vibration member 360 and checking whether the applied test current C flows through the vibration member 360 and the vibration transmission member 340 (that is, whether electrical conduction occurs). This is because electrical conduction would occur only when the vibration member 360 and the vibration transmission member 340 are in close contact.

Also, when the vibration member 360 and the vibration transmission member 340 are determined as being in close contact, the controller 210 may recognize the cartridge 10 as being coupled to the control main body 20. That is, when the cartridge 10 is coupled to the control main body 20, the controller 210 may recognize the coupling state of the cartridge 10 based on the fact that the two members 340 and 360 come in close contact when the cartridge 10 is coupled to the control main body 20.

Also, in a case in which the vibration member 360 and the vibration transmission member 340 are released from close contact, the controller 210 may recognize the cartridge 10 as having been removed from the control main body 20. In this case, the controller 210 may automatically stop the operation of the vibration member 360. This is because, when the vibration member 360 solely operates without a target to transmit vibrations to, a considerable amount of heat may be generated and cause damage to the expensive vibration member 360, or the control main body 20 may become hot and cause a user to get burned.

Meanwhile, the controller 210 may periodically or non-periodically determine whether the two members 340 and 360 are in close contact. For example, the controller 210 may automatically determine whether the two members 340 and 360 are in close contact according to a predetermined cycle to automatically recognize mounting of the cartridge 10. As another example, the controller 210 may periodically determine whether the two members 340 and 360 are in close contact during operation (e.g., smoking) of the aerosol generation device 1 to monitor a coupling state of the cartridge 10. As still another example, the controller 210 may determine whether the two members 340 and 360 are in close contact and recognize a coupling state of the cartridge 10 when a designated user input (e.g., power on, operation request, etc.) is received. If it is determined that the cartridge 10 is not coupled, the controller 210 may provide a message which informs the recognized result (e.g., an error message that informs of the non-coupling of the cartridge) in a form recognizable by the user. Here, the form recognizable by the user may include any form that is visually recognizable (e.g., displaying on a display, flickering of a light emitting diode (LED), etc.) aurally recognizable (e.g., voice, sound effects, etc.), or tactually recognizable (e.g., vibration, etc.).

Next, FIG. 10 is an exemplary view illustrating a cartridge recognition method according to a second embodiment of the present disclosure. Hereinafter, description will be given with reference to FIG. 10.

In the present embodiment, the vibration member 360 may be implemented using a piezoelectric element, and the controller 210 may use a piezoelectric phenomenon of the vibration member 360 to recognize a coupling state of the cartridge 10. That is, the controller 210 may recognize a coupling state of the cartridge 10 on the basis of an operation principle of the piezoelectric element that is capable of converting electrical energy into mechanical energy and vice versa.

More specifically, as illustrated, when the cartridge 10 is mounted on the control main body 20, as the lower end portion of the cartridge 10 comes in close contact with the vibration member 360, a pressure P may be applied to the vibration member 360. For example, the pressure P may be applied to the vibration member 360 as the vibration transmission member 340, which is disposed in the vicinity of the open lower end portion of the cartridge 10 and protrudes downward, comes in close contact with the vibration member 360. However, the scope of the present disclosure is not limited to the above example, and the cartridge 10 may also be designed so that a portion other than the vibration transmission member 340 applies the pressure P to the vibration member 360. When the pressure P is applied to the vibration member 360, due to the piezoelectric phenomenon, a voltage (that is, electrical energy) may be generated in the vibration member 360. Therefore, the controller 210 may measure the voltage (or power) generated in the vibration member 360 to recognize a coupling state of the cartridge 10 (e.g., whether the cartridge 10 is coupled, a degree of coupling of the cartridge 10, etc.).

In order to recognize a coupling state of the cartridge 10, the controller 210 may include a measurement device 211 configured to measure a voltage (or power). Here, the measurement device 211 may be implemented using a circuit element such as a voltmeter or may be implemented in other ways. The measurement device 211 may be implemented in any way as long as the measurement device 211 is able to measure a voltage (or power) generated in the vibration member 360.

In response to determining that a voltage measured through the measurement device 211 is a reference value or more, the controller 210 may recognize the cartridge 10 as being coupled to the control main body 20. Here, the reference value may be a predetermined fixed value or a variable value that varies according to situations. For example, the reference value may be a fixed value that is experimentally determined through a cartridge mounting experiment. As another example, the reference value may be a variable value that is adjusted on the basis of an amplitude of a voltage previously generated when the cartridge was coupled (mounted). For example, the controller 210 may increase or decrease an experimentally determined voltage value on the basis of the amplitude of a voltage generated upon coupling of the cartridge, thereby updating the reference value. Also, the reference value may be set as a single value or set as a range of values. In a case in which the reference value is set as a range of values, in response to determining that a measured voltage is within the set range, the controller 210 may recognize the cartridge 10 as being coupled to the control main body 20.

Conversely, in response to determining that a measured voltage is less than the reference value, the controller 210 may recognize the cartridge 10 as not being coupled to the control main body 20 (or as having been removed therefrom).

In some embodiments, the controller 210 may recognize a coupling state of the cartridge 10 also on the basis of a duration of a generated voltage in addition to the amplitude of the voltage. For example, the controller 210 may determine the cartridge 10 as being coupled only when a measured voltage is a reference value or more and the voltage has been generated for a predetermined amount of time or more. In this case, it is possible to address a problem in which the controller 210 mistakenly recognizes a coupling state of the cartridge 10 due to a voltage generated upon momentary contact of a specific object (e.g., a finger, an iron rod) with the vibration member 360.

Also, in some embodiments, the controller 210 may distinguish and recognize multiple types of cartridges 10 on the basis of a measured voltage. Specifically, a degree to which pressure is applied to the vibration member 360 upon mounting of the cartridge 10 may be designed to vary according to the type of the cartridge 10. For example, a degree to which the vibration transmission member 340 protrudes downward may be designed to vary according to the type of the cartridge 10. In this case, the controller 210 may recognize the coupled cartridge 10 as a first type of cartridge in a case in which a measured voltage is a first reference value or more and may recognize the coupled cartridge 10 as a second type of cartridge in a case in which a measured voltage is higher than or equal to a second reference value which is higher than the first reference value. According to the present embodiment, the controller 210 may accurately recognize a coupling state of the cartridge 10 and even the type of the cartridge 10 without an additional cartridge recognition sensor.

The cartridge recognition methods according to some embodiments of the present disclosure have been described above with reference to FIGS. 9 and 10. According to the above-described methods, a coupling state of the cartridge 10 may be accurately recognized without an additional cartridge recognition sensor. Therefore, since the aerosol generation device 1 does not require a cartridge recognition sensor, manufacturing costs may be reduced, and complexity of an internal structure of the aerosol generation device 1 may be further reduced.

The technical spirit of the present disclosure described above with reference to FIGS. 9 and 10 may be implemented with computer-readable code on computer-readable recording media. Examples of the computer-readable recording media may include removable recording media (a compact disc (CD), a digital versatile disc (DVD), a Blu-Ray disk, a universal serial bus (USB) storage device, a removable hard disk) or non-removable recording media (a read-only memory (ROM), a random access memory (RAM), a built-in hard disk). Computer programs recorded in the computer-readable recording media may be sent to other computing devices through a network, such as the Internet, and installed in the other computing devices so as to be used in the other computing devices.

All the components constituting the embodiments of the present disclosure have been described above as being combined into one body or being operated in combination, but the technical spirit of the present disclosure is not necessarily limited to the embodiments. That is, any one or more of the components may be selectively operated in combination within the intended scope of the present disclosure.

The embodiments of the present disclosure have been described above with reference to the accompanying drawings, but those of ordinary skill in the art to which the present disclosure pertains should understand that the present disclosure may be embodied in other specific forms without changing the technical spirit or essential features thereof. Therefore, the embodiments described above should be understood as being illustrative, instead of limiting, in all aspects. The scope of the present disclosure should be interpreted by the claims below, and any technical spirit within the scope equivalent to the claims should be interpreted as falling within the scope of the technical spirit defined by the present disclosure.

What is claimed is:

1. An ultrasonic-based aerosol generation device with mutually separable cartridge and a control main body coupled, the ultrasonic-based aerosol generation device comprising:

a liquid reservoir configured to store a liquid aerosol-forming substrate;

a vibration element configured to provide ultrasonic vibrations to the stored liquid aerosol-forming substrate to form an aerosol; and a porous member disposed apart from the vibration element and including a plurality of holes, wherein the aerosol is formed as the stored liquid aerosol-forming substrate passes through the plurality of holes due to the provided ultrasonic vibrations, wherein the vibration element comprises:

a vibration member configured to generate the ultrasonic vibrations; and a vibration transmission member configured to transmit the generated ultrasonic vibration to the stored liquid aerosol-forming substrate, wherein the vibration transmission member, the liquid reservoir, and the porous member are included in the cartridge, wherein the vibration member and a controller configured to control the aerosol generation device are included in the control main body, wherein the cartridge is replaceable, and wherein the porous member is disposed facing and spaced apart from a vibrating surface of the vibration element.

2. The ultrasonic-based aerosol generation device of claim 1, wherein:

the vibration member and the vibration transmission member each include a flat portion; and as the cartridge is coupled to the control main body, flat portions of the vibration member and the vibration transmission member come in close contact with each other.

3. The ultrasonic-based aerosol generation device of claim 2, wherein:

the vibration transmission member is disposed in a vicinity of an open lower end portion of the cartridge, and the flat portion of the vibration transmission member protrudes downward;

the flat portion of the vibration member is disposed in an open form at a portion where the control main body is coupled to the cartridge; and the flat portions of the vibration member and the vibration transmission member are coupled to each other as the lower end portion of the cartridge is coupled to the control main body.

4. The ultrasonic-based aerosol generation device of claim 1, wherein:

the vibration member and the vibration transmission member are made of an electrical conductor; and the controller determines whether the vibration member and the vibration transmission member are in close contact based on whether electrical conduction occurs between the vibration member and the vibration transmission member.

5. The ultrasonic-based aerosol generation device of claim 1, wherein:

the vibration member includes a piezoelectric element; and the controller determines whether the vibration member and the vibration transmission member are in close contact based on a voltage generated in the vibration member.

6. The ultrasonic-based aerosol generation device of claim 1, wherein a thickness of at least a portion of the vibration transmission member is in a range of 0.01 mm to 1 mm.

7. The ultrasonic-based aerosol generation device of claim 1, wherein a separation distance between the vibration element and the porous member is in a range of 0.1 mm to 2 mm.

8. The ultrasonic-based aerosol generation device of claim 1, wherein a thickness of the porous member is in a range of 0.01 mm to 2 mm.

9. The ultrasonic-based aerosol generation device of claim 1, wherein a size of each hole is in a range of 1 μm to 500 μm.

10. The ultrasonic-based aerosol generation device of claim 1, wherein each hole is formed in a shape of an orifice.

\* \* \* \* \*